United States Patent [19]
Seifert et al.

[11] Patent Number: 5,721,120
[45] Date of Patent: Feb. 24, 1998

[54] METHOD OF DISRUPTING CULTURED CELLS USING AN IMPINGING JET DEVICE

[75] Inventors: Douglas B. Seifert, Hatfield; Frank S. Leu, Lansdale, both of Pa.

[73] Assignee: Merck & Co., Inc., Rahway, N.J.

[21] Appl. No.: 724,802

[22] Filed: Oct. 2, 1996

[51] Int. Cl.[6] .................. C12D 21/06; C12D 21/02; C12N 5/00; C12N 7/00
[52] U.S. Cl. .................. 435/693; 435/240.3; 435/235.1; 435/285.1
[58] Field of Search .................. 435/69.3, 240.5, 435/235.1, 285.1

[56] References Cited

U.S. PATENT DOCUMENTS

| | | | |
|---|---|---|---|
| 3,309,032 | 3/1967 | Filz et al. | 241/301 |
| 5,360,736 | 11/1994 | Provost et al. | 435/240.21 |

FOREIGN PATENT DOCUMENTS

| | | |
|---|---|---|
| 0 335 188 | 10/1989 | European Pat. Off. . |
| 346 862 | 2/1905 | France . |
| 877 898 | 9/1961 | United Kingdom . |

OTHER PUBLICATIONS

Engler, et al. :Effects of organism type and growth conditions . . . : Biotech. Letters: vol. 3, No. 2: pp. 83–88, 1981.

Primary Examiner—Lynette F. Smith
Assistant Examiner—Brett Nelson
Attorney, Agent, or Firm—Joanne M. Giesser; Jack L. Tribble

[57] ABSTRACT

A novel method of disrupting cells which do not have a cell wall comprises passing suspended cells through a low pressure impinging jet device. This method disrupts the cells, but does not harm the cell products which are liberated.

10 Claims, 1 Drawing Sheet

METHOD OF DISRUPTING CULTURED CELLS USING AN IMPINGING JET DEVICE

FIELD OF THE INVENTION

This invention relates to a method for the disruption of cells grown in culture by using opposing jet streams operating at a low pressure to create a disruptive fluid shear which is powerful enough to disrupt the cells, but not so powerful as to destroy their contents.

BACKGROUND OF THE INVENTION

Many biotechnological and fermentation processes require large amounts of cells to be grown in a bioreactor, and then disrupted to liberate desirable products. Cell disruption can be accomplished by mechanical, chemical, biological, or physical means. Many protocols favor mechanical disruption processes since it is highly desirable to eliminate the need for additional reagents (detergents, enzymes, or osmolarity effectors) and avoid difficult to scale up physical methods such as freeze/thaw.

A number of mechanical methods have been developed to disrupt microorganisms. These methods generally rely on fluid shear and/or compression to rupture the cell wall and membrane. However, not all biotechnological and fermentation processes use microorganisms. Animal cells are becoming a common the host cell of choice. Since animal cells are larger and have a fragile membrane, much less energy input is required to effect the desired cell disruption. Many of the commercial systems designed for microbial systems are not suitable for use with animal cells.

Rotor/stator devices having a cylindrical rotor turning at high speed concentrically inside a stator may be used to disrupt animal cells. These devices create a steep velocity gradient in the annular region generating sufficient shear stress in the fluid to disrupt the cells. A similar device called the CHAIKOFF PRESS has a cylinder and a piston of a slightly smaller diameter. Movement of the piston creates high shear in the fluid within the annular space, causing cell rupture. This type of device is also referred to as a "douncer" and has been used for the disruption of MRC-5 diploid lung cells infected with Varicella. However, these methods are only workable at the laboratory scale, and are not amenable to scale-up for manufacturing.

Ultrasonics or sonication disrupts cells by creating high shear stress regions in the fluid through the process of cavitation. Oscillating acoustic waves (~20 kHz) create pressure pauses in the fluid. Vapor bubbles formed in the low pressure region, collapse upon entering the high pressure region causing high energy shock waves. As the shock wave moves radially from the initial cavitation site, high shear stresses are generated as well as heat as the energy dissipates in the fluid.

A continuous flow sonication device has been used to disrupt MRC-5 diploid lung cells containing Varicella virus. The region in close proximity to the origin of the shock wave is of sufficient energy to destroy Varicella infectivity. Therefore, the amount of virus infectivity lost depends on the number of nucleation sites generated per unit volume fluid which is related to the energy input into the fluid. However, the continuous sonication process also results in a 5° to 10° C. temperature rise in the process fluid, which increases the degradation rate of the virus. Sonication energy input can be lowered to increase post sonication titers; however, less disruption results in greater losses across the clarifying filters. An optimization exists between infectious titer loss due to sonication and the degree of cell disruption required for high titers post clarification.

In another prior process, freeze/thaws are used to maximize the release of Rotavirus from culture. This method, while useful, is difficult to implement in manufacturing.

Two impinging jet methodologies are known: impingement of a fluid jet on a plate and impingement on an opposing jet. The impinging region produces a micromixing zone where the shear is controlled by the linear velocity of the jet. These devices have been used for the disruption of microbial cells. Commercially, the MICROFLUIDIZER, one such inpinging jet device, uses an interaction chamber where two jet streams impinge on one another at linear velocities up to 200+ m/s. The mode of disruption are reported as cavitation, fluid shear and impact. However, this device is not suitable for use with animal cells because not only are cells disrupted, but their contents are damaged as well.

It would be desirable to have a device which efficiently disrupts animal cells and releases the cell content without damage.

DETAILED DESCRIPTION OF THE INVENTION

This invention relates to a novel method of disrupting cultured cells which lack a cell wall comprising passing cells suspended in a suspension fluid through a low pressure impinging jet device.

One of the benefits of this method is that products which are made by the cultured cells may be released without destruction of those products by subjecting the cells to a low pressure fluid controlled shear force delivered by an impinging jet device. Therefore another aspect of this invention is a method of harvesting a cell product contained within a cell which does not have a cell wall comprising:

a) culturing cells under culture conditions in a culture medium until the cell product is produced;

b) suspending the cells in a suspension fluid;

c) passing the suspended cells through a low pressure impinging jet device so that the cells are disrupted at a pressure of from about 5 to 100 psi and the cell product is released; and d) recovering the released cell product.

The method of this invention may be broadly applied to any cell which lacks a cell wall or which has had its cell wall removed. While animal cells are preferred, this method works equally well with other cells, such as plant or fungal protoplasts and bacterial spheroplasts. The only requirement is that the cells be amenable to cell culture, and it is preferred that the cells be amenable to a large scale culture. Examples of suitable animal cells include VERO cells, CHO cells, and diploid fibroblast cells such as MRC-5 cells. Examples of suitable plant protoplasts include Nicotiana, Petunia, Zea, Brassica, and interspecial hybrids. The cells lines may be immortalized or not, and they may be cultivated in either a stationary or in a suspension culture. None of the particular culture parameters are critical to the method of this invention.

The method of this invention may be used to recover virtually any type of product which is made using the cultured cells. Examples of such products include: naturally occurring products, such as proteins; polysaccharides; recombinant proteins, including antibodies and enzymes; and viruses. In a preferred embodiment of this invention, animal cells are used as host cells for the production of viruses which are used in the manufacture of vaccines. Thus, this invention comprises method of harvesting a virus grown in an animal cell comprising:

a) culturing animal cells infected with the virus;
b) suspending the animal cells containing the virus in a suspension fluid;
c) passing the suspended animal cells through a low pressure impinging jet device so that cells are disrupted and the virus is released; and
d) harvesting the released virus.

In one particularly preferred embodiment, MRC-5 human diploid lung cells infected Varicella Zoster Virus, particularly with the OKA strain of Vailcella Zoster Virus, are disrupted to harvest virus used to prepare a live virus vaccine, VARIVAX®.

BRIEF DESCRIPTION OF THE FIGURES

The cells are cultured as is customary for the particular cell. After a suitable culture period, the cells are released from their substrate (if they are anchored), suspended in a fluid. The fluid may be the same or similar to that used to culture the cells, or it may be a stabilizer. For purposes of this invention, the composition of the suspension fluid is not critical. Next, the suspended cells are processed through an impinging jet device such as that shown in FIG. 1. Referring now to FIG. 1, fluid shear is preferably generated by impinging two opposing jet streams 111 and 101 at a controlled linear velocity in a small chamber 120. The device is preferably operated in a continuous mode with the input stream split into a two jet streams 100, 110 and an outlet stream 130 draining the chamber. It is desirable that nozzles 111 and 101 be placed in close proximity to each other, i.e. less than one inch apart, and more preferably approximately ⅛th to ⅜ths of an inch apart in order to maximize the fluid shear.

Figure 1:
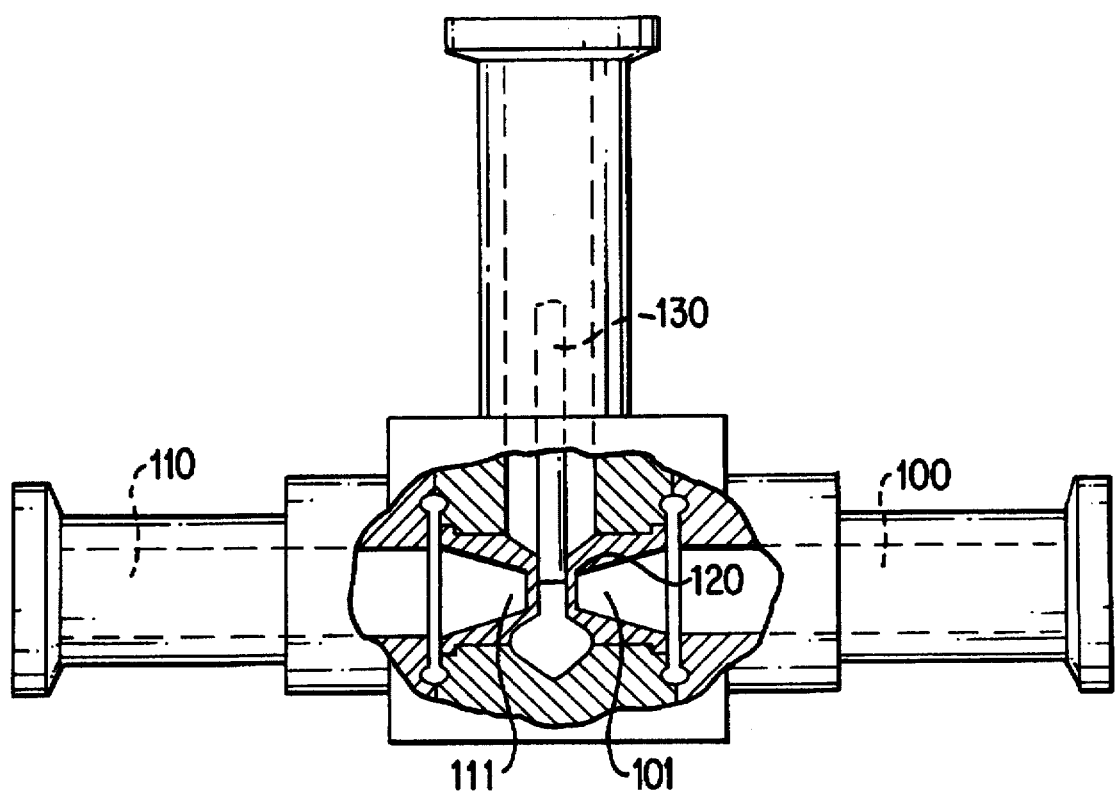
FIG. 1 is a drawing of an impinging jet device which may be used in the method of this invention.

A critical aspect of this method is that the device is operated at a low pressure, in a non-cavitating mode, preferably less than about 150 psi, and more preferably less than about 100 psi. The low operating pressure results in a gentle disruption-cells are preferably ruptured at a very low pressure, from about 5 to about 100 psi. This is one of the features which distinguishes the instant method from those of the prior an. For example, a commercially available impinging jet cell disrupter, sold under the tradename MICROFLUIDIZER® by Microfluidics International Corp., Newton, Mass., reports disruption of animal cells at 2,000 psi. At this high pressure, cavitation and its damaging effects are likely to occur.

The linear jet velocity at the point of impingement is also a critical aspect of this invention since it dictates the disruptive force. For this method, it is preferred that the linear jet velocity be approximately 5 to 50 m/s, and preferably 10 to 30 m/s.

The method of this invention has been designed specifically for disruption of cells without cell walls, where a lower energy input is delivered in a controlled way. It is difficult for a high pressure device such as an homogenizer or MICROFLUIDIZER®, an impinging jet device, which are designed to deliver up to 15,000 and 40,000 psi, respectively, to deliver precise control at low pressures well below their respective design specifications whereas the method of this invention preferably uses a device which optimally runs at a low pressure.

The impinging jet process of this invention has been shown to provide adequate cell breakage for high filtration yields with negligible loss of infectious titer. In preliminary studies the impinging jet provided superior yields to the freeze/thaw approach.

The method of this invention has a number of advantages over the current methods of cell disruption. First, the device is simple in design and does not require a piston pump nor cooling device, avoiding problems associated with these types of components. The low pressure operating system has the further advantage of conveniently allowing a low pressure processing pump (lobe, or diaphragm) or a relatively low pressure vessel to be used to drive the fluid.

Due to its lower operating pressure, there is only a negligible amount of heat (<0.1° C.) generated during the disruption process.

The device is quite small in size so it can be incorporated into standard process piping connecting two vessels.

The impinging jet device disrupts the cells by fluid shear created by micromixing in a well defined impingement zone. Cavitation does not occur under the disruption conditions used. Heterogeneous zones of damaging high shear stress common to cavitation based disruption mechanisms are avoided.

The impinging jet device is scaleable. The volumetric processing rate at a given linear velocity can be increased by increasing the jet orifice.

Provides a controlled fluid shear based disruption for high recovery of labile biomolecules or viruses.

The device is sanitary in design and uses commercially available nozzle technology for consistent fabrication, and can be incorporated directly into standard process equipment. Further, the device can be sterilized in place.

High pressure operation >200 psi and the associated issues are avoided.

In a preferred embodiment, the impinging jet cell disruption method of this invention can be used for high yield recovery of Vailcella Zoster Virus, other viruses or intracellular proteins from animal cells. After disruption, cell debris is separated from the associated virus particles by clarifying filter, and the resultant virus preparation is frozen until further processing into the vaccine.

The following non-limiting examples are presented to better illustrate the invention.

EXAMPLE 1

Roller bottles containing attached MRC-5 cells infected with varicella virus are rinsed, dispensed with 40 ml of either 1.0× or 1.5× PGSE stabilizer, and harvested from roller bottles by mechanically scraping the cell sheet from roller bottles using a robotic arm. The cell slurry is withdrawn from the roller bottle, collected in a vessel, and frozen to –60° C. Prior to processing, an impinging jet apparatus is calibrated to determine the pressure required to give the desired linear velocity, then sterilized. The vessels containing frozen harvested material are thawed, pooled, and placed in a pressure vessel connected to the impinging jet apparatus. The contents of the pressure vessel are pressurized to give a linear velocity through the jets of 22.5 m/s (1.0× PGSE) or 25.0 m/s (1.5× PGSE). The jetted material is transferred back in the pressure vessel for a second pass.

EXAMPLE 2

Alternatively, two jets in series can be used. The disrupted cells are then clarified by filtration through polypropylene depth filters. Potency is assayed through a plaque assay. Particle size analysis using a Elzone particle analyzer is also completed.

What is claimed is:

1. A method for the disruption of cultured cells which lack a cell wall comprising passing cells suspended in a culture fluid through a low pressure impinging jet device.

2. A method according to claim 1 wherein the cells are animal cells.

3. A method according to claim 2 wherein the animal cells are selected from the group consisting of: VERO cells, CHO cells, and diploid fibroblast cells.

4. A method according to claim 1 wherein the jet device ruptures the cells at a pressure of about 5 to 100 psi.

5. A method of harvesting a cell product contained within a cell which does not have a cell wall comprising:

a) culturing cells in a culture medium under culture conditions suited to bring about the production of the desired cell product;

b) suspending the cells in suspension fluid;

c) passing the suspended cells through a low pressure impinging jet device so that the cells are disrupted at a pressure of from about 5 to 100 psi and the cell product is released; and d) recovering the released cell product.

6. A method according to claim 5 wherein the cell is an animal cell.

7. A method according to claim 6 wherein the product is selected from the group consisting of a naturally occurring protein, a recombinant protein, and a virus.

8. A method of harvesting a virus grown in an animal cell comprising:

a) culturing animal cells infected with the virus;

b) suspending the animal cells containing the virus in a suspension fluid;

c) passing the suspended animal cells through a low pressure impinging jet device so that cells are disrupted and the virus is released; and d) harvesting the released virus.

9. A method according to claim 8 wherein the animal cells are MRC-5 diploid lung cells.

10. A method according to claim 9 wherein the virus is varicella virus.

* * * * *